United States Patent [19]

de Lasa

[11] Patent Number: 4,929,798
[45] Date of Patent: May 29, 1990

[54] PSEUDOADIABATIC REACTOR FOR EXOTHERMAL CATALYTIC CONVERSIONS

[75] Inventor: Hugo I. de Lasa, London, Canada

[73] Assignee: Canadian Patents and Development Limited, Ontario, Canada

[21] Appl. No.: 288,158

[22] Filed: Dec. 22, 1988

Related U.S. Application Data

[60] Division of Ser. No. 189,404, Apr. 27, 1988, which is a continuation of Ser. No. 702,576, Feb. 19, 1985, abandoned.

[30] Foreign Application Priority Data

Mar. 5, 1984 [CA] Canada ................................. 448807

[51] Int. Cl.$^5$ .............................................. C07C 1/20
[52] U.S. Cl. .................................... 585/922; 422/109; 422/119; 422/197; 585/402; 585/403; 585/636; 585/640; 585/920
[58] Field of Search ............... 585/640, 402, 403, 636, 585/920, 921, 922; 422/109, 119, 197, 201, 312, 180

[56] References Cited

U.S. PATENT DOCUMENTS

| | | | |
|---|---|---|---|
| 2,803,440 | 8/1957 | Simpelaar | 422/197 |
| 3,547,188 | 12/1970 | Kurmlein | 422/197 |
| 3,566,961 | 3/1971 | Lorenz et al. | 422/197 |
| 3,807,963 | 4/1974 | Smith | 422/197 |
| 4,101,287 | 7/1978 | Sweed et al. | 422/197 |
| 4,235,281 | 11/1980 | Fitch et al. | 422/197 |
| 4,303,618 | 12/1981 | Fukui et al. | 422/190 |
| 4,305,910 | 12/1981 | Kudo et al. | 422/197 |
| 4,336,770 | 6/1982 | Kaneko et al. | 122/266 |
| 4,363,787 | 12/1982 | Yoon | 422/201 |
| 4,378,336 | 3/1983 | Yoon | 422/201 |

Primary Examiner—Asok Pal
Attorney, Agent, or Firm—Shoemaker and Mattare Ltd.

[57] ABSTRACT

A multitubular catalytic reactor for exothermal catalytic reactions comprises a bundle of parallel tubes all of the same length and a catalyst within the tubes. The tube bundle has an inlet side and an outlet side. Devices are provided for introducing separately reactants to within the tubes of the reactor and coolant to the channels defined between adjacent tubes of the bundle. The coolant is introduced into the channels co-currently with the direction of flow of the reactants. The products are withdrawn from the tubes independently of the coolant. The reactor is particularly adapted to a single stage conversion of methanol into gasoline boiling point range constituents using crystalline aluminosilicate catalysts.

1 Claim, 3 Drawing Sheets

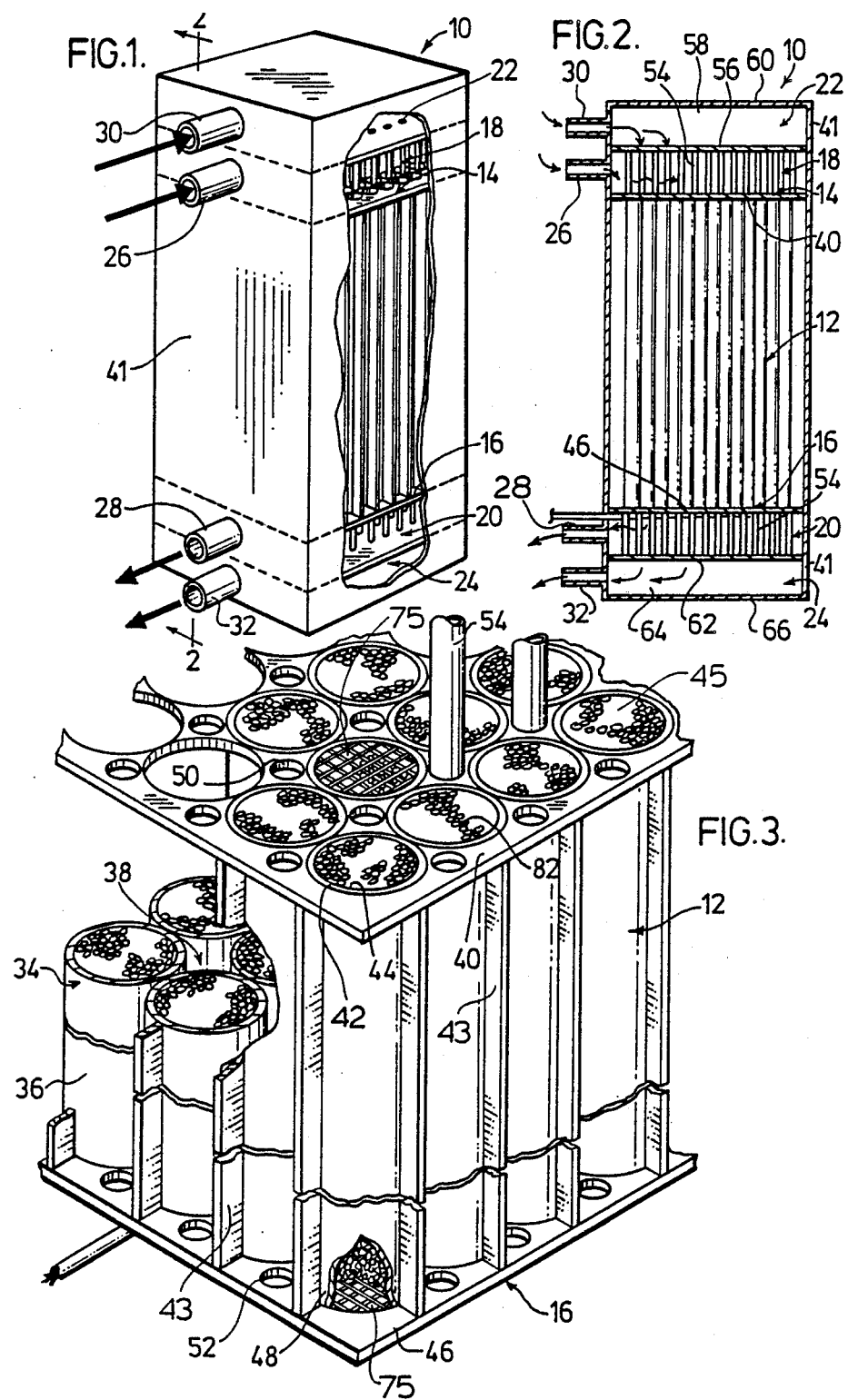

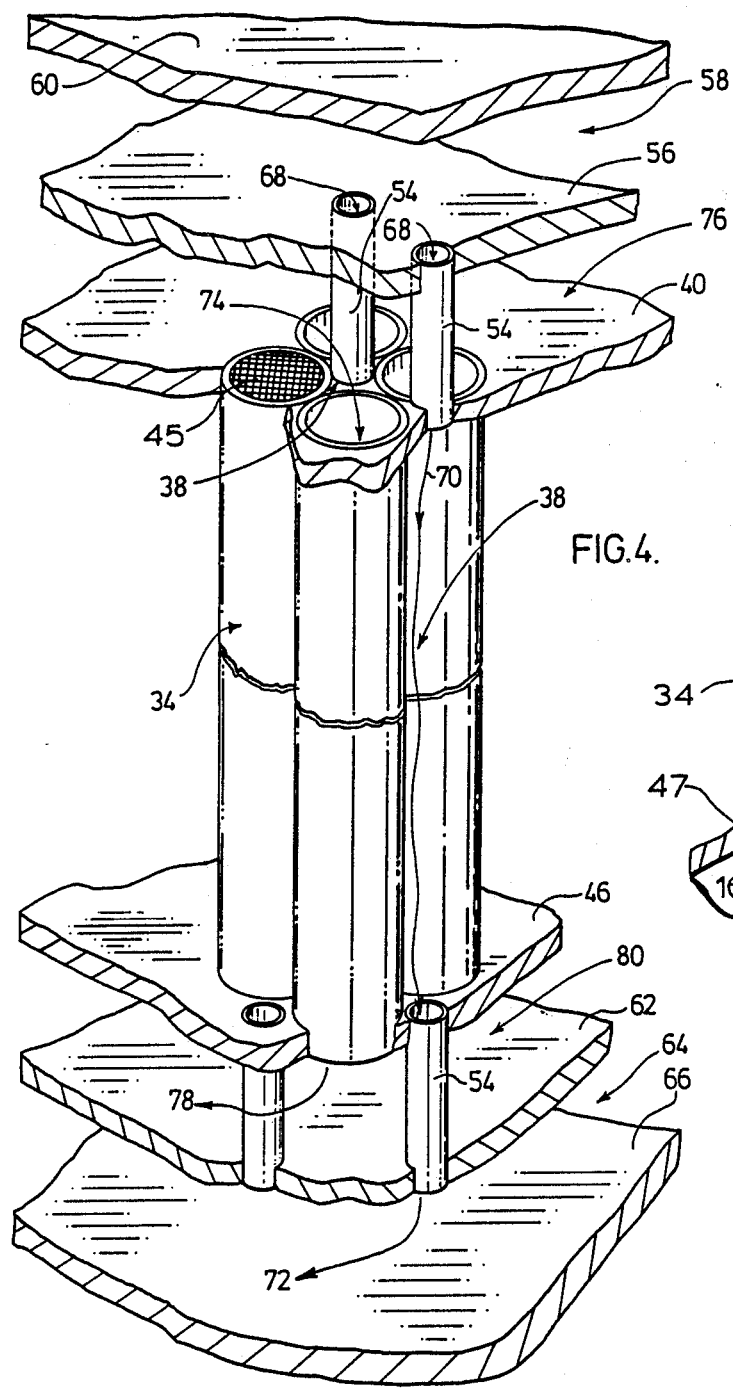
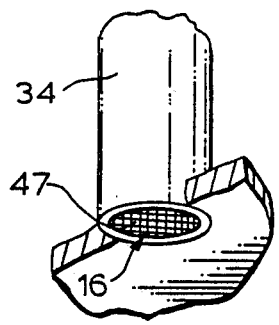
FIG.4.
FIG.4A.

PSEUDOADIABATIC REACTOR FOR EXOTHERMAL CATALYTIC CONVERSIONS

This is a division of application Ser. No. 189,404, filed April 27, 1988, which is a continuation of application Ser. No. 06/702,576 filed 02/19/85, now abandoned.

FIELD OF THE INVENTION

This invention relates to catalytic reactors and processes therefore as they relate to exothermal catalytic reactions, and more particularly to multitubular reactors designed in a manner to operate in a regime defined as pseudoadiabatic.

BACKGROUND OF THE INVENTION

Solid catalysts have been used in a variety of systems principally fixed bed and fluidized bed reactors for effecting various conversions. A prominent use of catalysts is in the catalytic cracking of hydrocarbon feeds of the petroleum industry. Another example of late is the use of aluminosilicate catalysts for use in the exothermic conversion of alcohols and their ethers to aromatics and higher hydrocarbons of the gasoline boiling point range.

Extensive effort has been devoted to the development of the aluminosilicate catalyst to improve the efficiency of the conversion and in dealing with the heat generated by the highly exothermic reaction. In an attempt to control the temperature of reaction, two-stage catalytic reactors have been devised as disclosed in U.S. Pat. Nos. 3,931,349; 3,928,483; and 4,058,576. These patents involve the use of diluents in controlling the temperature of the reaction and also the use of heat exchange medium as disclosed in U.S. Pat. No. 4,058,576 for controlling the temperature of the reaction within the range of 600° K. to 830° K. These systems have the significant drawback in that a dual-or triple-stage system of catalytic beds must be developed. Usually the first stage involves a condensation reaction using an acidic catalyst, followed by the use of crystalline aluminosilicate zeolite catalysts for converting the condensed products into the gasoline boiling point range constituents. These reactors involve recycle which can result in the increased production of aromatics, particularly durenes which can crystallise out of the gasoline mixture and cause problems in use.

Another approach in controlling the temperature of the reaction is to use a fluidized bed of the catalyst as disclosed in U.S. Pat. Nos. 4,046,825; 4,138,440; 4,197,418; and 4,251,484. By using a fluidized bed of the zeolite catalyst, in particular the ZSM-5 type, conversion of methanol to gasolines is accomplished. However, the highly exothermic reaction has to be controlled in a manner such as disclosed in the U.S. Pat. No. 4,138,440 where the reaction temperature is controlled by the heat of vaporization of the liquid methanol charged to the system. In U.S. Pat. No. 4,197,418 the use of a complex baffle system restricts the upflow reactant bubble growth to in turn control the mass transfer and the reactant conversion. In U.S. Pat. No. 4,251,484 the use of heat exchange tubes in the fluidized bed of the catalyst maintains a hydraulic diameter within the desired limits to control the reaction. These systems thereby complicate the fluidized bed approach and do not always ensure the control of temperature throughout the fluidized bed.

Fixed bed catalytic reactors are favoured compared to the more difficult to control fluidized bed reactors. However, on an industrial scale fixed bed reactors as used in exothermic catalytic conversions have the problem of developing "hot spots" in various regions of the fixed bed reactor. This phenomenon is known as parametric sensitivity where the chemical reactor is very sensitive to the changes of operating variables such as reactant inlet temperature and reactant inlet partial pressure. Complex temperature sensing systems are required in the industrial scale catalytic fixed bed reactors in order to avoid catalyst damage, safety hazards and poor process selectivities in preventing hot spots in the reactor. Although the use of fluidized beds generally overcomes this problem, the fluidized beds involve complex gas flow patterns and non-uniform solid residence time. This makes the prediction of industrial dense fluidized bed performance a difficult task and complicates their generalized application and scaleup for use in industry. Therefore the fixed bed system is generally favoured. However, in an industrial sense the normal approach as disclosed in the above-noted patents is a two-stage reactor system, for example as particularly applied to the conversion of methanol into gasoline boiling point constituents. The reactor operates on a 7 to 9 recycle ratio, operating at 30 atm. and a temperature in the range of 316° to 450° C. to control the heat evolved in an adiabatic fixed bed reactor. In this system a significant methanol bypass or aromatic products backmix is taking place as a consequence of the recycle which may affect selectivity and increase the undesirable durene fractions in the gasoline.

In an effort to improve upon the fixed bed catalytic reactor involving highly exothermic catalytic conversions, a reactor model was developed and reported by A. Soria Lopez, H. de Lasa, J. A. Porras, *Chemical Engineering Science* Vol. 36, p. 285 1981 concerning a reactor which demonstrated pseudoadiabatic properties. The reactor model as investigated and disclosed in that paper involves the co-current flow of coolant along the outside of a tube containing a fixed bed of particulate catalyst for the catalytic oxidation of orthoxylene. That reactor simulation based on a unidimensional model, first approximation that assumed that temperatures change only with the axial position, suggested that the use of a co-current flow of coolant within a certain range relative to a particular concentration of reactants avoided hot spots developing within the reactor tube.

According to this invention a multitubular catalytic reactor has been designed for particular use with exothermal catalytic reactions which overcomes the problems of the above prior systems. The system may be particularly adapted for use in the exothermic catalytic conversion of lower alcohols and their ethers to gasoline boiling point range constituents.

According to an aspect of the invention, a multitubular catalytic reactor for exothermic reactions of gasoline constituent forming reactants comprises a bundle of parallel tubes and a confined volume of catalysts within each of the tubes along their length. Each of the tubes is continuous along its length and independent of all other tubes. The tubes have effective reactive regions therein, all of essentially the same length, as defined by a consistent confined volume of catalyst in each of the tubes. The tube bundle has an inlet side and an outlet side. A reactant header is in communication with the inlet side of the tube bundle and a product header is in communication with the outlet side of the tube bundle. An inlet to the reactant header for introducing reactants into the tubes is provided, and an outlet for the product header for withdrawing products therefrom is also provided. Means defines a discrete channel along adjacent tubes of the bundle to provide thereby a plurality of channels through the bundle where each tube of the bundle is in contact with coolant flowing in one or more of the channels. The plurality of channels have an inlet side and an outlet side. Means is provided within the reactant header for isolating the flow of coolant through the reactant header into the inlet side of the plurality of channels. An upstream coolant header is provided outside of and adjacent the reactant header. The upstream coolant header has an inlet for introducing coolant to the individual channels via the coolant flow isolating means in the reactant header to provide coolant flow in the channels co-current with the flow of the reactants in the tubes. Means is provided within the product header for isolating flow of coolant through the product header as coolant emerges from the outlet side of the plurality of channels. A downstream coolant header is provided outside of and adjacent the product header. The downstream coolant header has an outlet for withdrawing coolant from the individual channels via the coolant flow of isolation means in the product header.

BRIEF DESCRIPTION OF THE DRAWINGS

Preferred embodiments of the invention are shown in the drawings wherein:

FIG. 1 is a perspective view of the multitubular catalytic reactor according to a preferred embodiment of the invention;

FIG. 2 is a section taken along line 2—2 through the reactor of FIG. 1;

FIG. 3 is a perspective view of a portion of the tube bundle of the reactor;

FIG. 4 is a perspective view of a section of the tube bundle showing the isolated flows of reactants, products and coolant;

FIG. 4A is a perspective view of the bottom of a tube of the tube bundle;

DETAILED DESCRIPTION OF THE PREFERRED EMBODIMENTS

Figure 5:
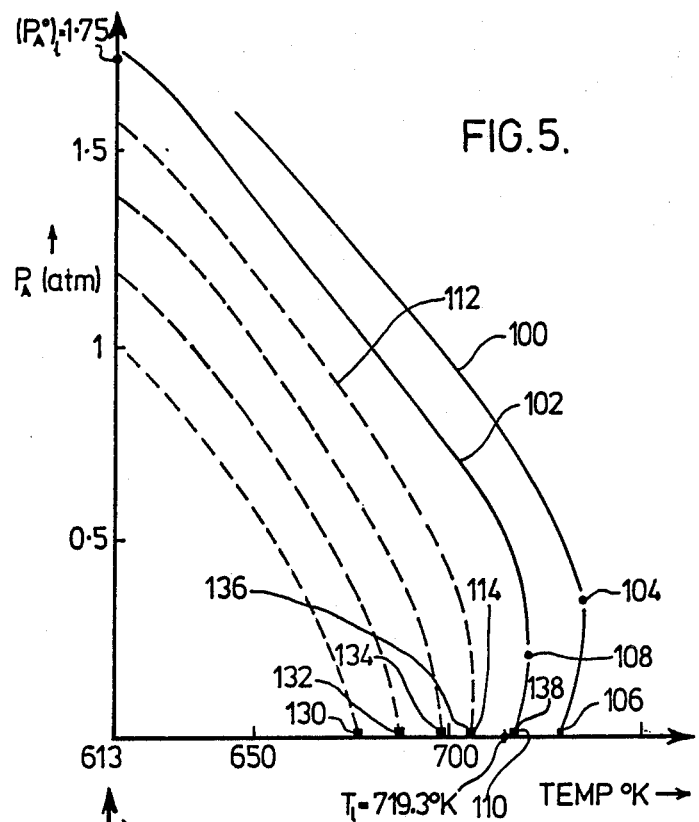
FIG. 5 is a plot of the partial pressure of the reactant versus the temperature within the reactant tube for the conversion of methanol over a ZSM-5 catalyst in the reactor of FIG. 1.

The multitubular reactor as shown in the drawings is designed to provide a pseudoadiabatic reactor operation. This term is selected to indicate that the temperature within the reactor tubes steadily increases through the reactor length with a maximum temperature at the reactor exit. This condition is characteristic of adiabatic reactors, where the wall heat transfer coefficient is normally zero. However, it is to be appreciated that there is in the pseudoadiabatic operation heat transferred from the reactor tubes through their walls into the coolant flowing co-currently along the exterior of the reactor walls. As reported in the Soria Lopez, de Lasa and Porras periodical, they indicated that co-current operation offered peculiar features for controlling and shifting the "hot spots" towards the exit of the reactor tubes. It has been found that by employing a co-current coolant reactant flow pattern that:

1. for a given inlet reactant partial pressure there is a range of coolant flows between $Wc_{max}$ and $Wc_{min}$ that leads to pseudoadiabatic conditions;
2. for a given Wc there is a $p_A°$ domain below a critical value of $(p_A°)_1$ where pseudoadiabatic operation takes place.

In the above formulations $p_A°$ = partial pressure of reactant at the entrance to the reactor, Wc = cooling medium mass flow rate and $(p_A°)_1$ = the limiting critical value for the partial pressure of the reactant which cannot be exceeded to obtain the pseudoadiabatic operation for a particular co-current flow rate of coolant.

By developing the rate of reactions, heat transfer coefficients and other parameters on an experimental basis, the maximum partial pressure for the reactants, $(p_A°)_1$ for a particular coolant flow rate can be determined in providing pseudoadiabatic operation of the reactor, whereby the exit temperature effectively becomes the "hot spot" for the reactor. This arrangement, therefore necessitates only a temperature sensor at the reactor exit to provide the required information for reactor control and operation. Due to the symmetry under pseudoadiabatic operation of the temperature and reactant concentration profiles, the profiles are identical for the different tubes of the bundle of the multitubular reaction, it is possible that a single temperature sensor may be needed in providing the necessary reactor monitoring. This reactor system thereby provides a controlled reaction which avoids catalyst damage and significant loss of the main product through secondary reactions. Another important matter of the pseudoadiabatic operation consists of the fact that only small radial temperature differences could be expected at the outlet of each of the tubes of the bundle. Thus reactor instrumentation is simplified and in fact a single thermocouple may be located at the centre of the outlet section of the tube bundle to provide the temperature readings very close to the average temperatures to ensure safe operation. This feature is also assured by designing the multitubular reactor to define discrete individual channels between adjacent tubes of the reactor configuration. This provides a plurality of channels in the tube bundle through which the coolant flows co-currently and exchanges with the particular tubes. Intermixing of the coolant between channels is avoided which would normally result in cross flow tubular reactor arrangements and arrangements which involve counterflow of coolant such as disclosed in U.S. Pat. No. 4,058,576. In that respect, de Lasa, H.; Mok, L. K.; Soria Lopez, A.; *Proceedings World Chemical Engineering Conference*, Montreal (1981) have shown the practical complexities of predicting "hot spots" in multitubular catalytic reactors where the coolant is circulated in a cross-flow pattern.

The pseudoadiabatic reactor configuration according to this invention is useful in many exothermic catalytic conversions which include the conversion of methanol to gasoline boiling point range constituents. The reactor may also be used in reactions such as the oxidation of orthoxylene and the oxidation of ethylene as conducted over a suitable particulate catalyst fixed within the tubular reactor. The reactor arrangement does not require recycle or the like in controlling the temperature of the reaction so that accurate control of the gas/solid contact times and of the "hot spots" within the reactor when running a diversity of exothermal catalytic reactions can be realized. Thus the reactor design can be used to replace many catalytic reactors involving dense bed fluidized systems or fixed bed reactors with hard to control internal "hot spots". The reactor design can be readily used in the various transformations of coal, natural gas and bio mass into gasoline.

Looking to the reactor of FIGS. 1 and 2 as particularly adapted in the catalytic conversion of methanol into gasoline, the reactor 10 is preferably vertically oriented and comprises a bundle of parallel tubes. Although the vertical orientation of the reactor with inlet at the top is preferred, it is appreciated that the flow direction can be reversed or the reactor may be slanted towards the horizontal. When the reactor is slanted, care must be taken to ensure that no air pockets form in the coolant channels. A reactant header 18 is provided at the inlet side 14 of the tube bundle and a product header 20 is provided at the outlet side 16 of the tube bundle. An upstream coolant header 22 in association with the reactant header 18 directs coolant to the reactor. A downstream coolant header 24 in association with the product header 20 removes coolant from the reactor 10. An inlet 26 is provided for the reactant header which introduces reactant thereto which in turn flows within the tubes of the tube bundle 12. An outlet 28 is provided on the products header to withdraw reactants which emerge from the tube bundle for subsequent processing. Inlet 30 is provided for the coolant as introduced to the header 22 for distribution through the reactor 10. Outlet 32 is provided on downstream coolant header 24 to withdraw coolant from the reactor which may be heat exchanged with the reactants or in any other manner treated for recirculation as coolant through inlet 30.

The tube bundle of the reactor of FIG. 1 is shown in more detail in FIG. 3. It is appreciated that various tube shapes are usable in the bundle. Regardless of the tube shape, provision is made to define the discrete channels between tubes for the coolant flow. Each tube 34 of the reactor extends parallel with all other tubes of the bundle 12. The exterior surface 36 of each tube abuts the exterior surface of adjacent tubes of the bundle to provide a closely packed arrangement. The tubes 34 are generally uniform in cross section so that abutting adjacent tubes define a discrete individual channel 38 which extends the length of the reactor tube bundle and is independent of the channels 38 defined by other sets of tubes.

An exterior shell 41 envelopes the tube bundle 12 where barrier devices 43 provide barriers between the periphery of the exterior tubes of the bundle and the interior of the shell 41. Barrier devices 43 are provided on each external tube of the tube bundle and thereby define channels about the periphery of the tube bundle between the shell and the tube bundle periphery and through which coolant also co-currently flows.

In order to isolate the flow of reactants through the tubes 34 from the flow of coolant, a special header arrangement is provided. The inlet side 14 of the tube bundle has a plate 40 into which the tube ends 42 extend to thereby isolate the channels 38 between the tubes from the tube interior 44. Similarly, at the outlet end 16 of the tube bundle, a plate 46 is positioned and into which the tube ends 48 extend to isolate coolant which flows out of the channels from the interior 44 of the tubes. The inlet plate 40 has a plurality of apertures 50 which extend through the plate and communicate with the respective channels. Similarly, with the lower plate 46, a plurality of apertures 52 extend through the plate to communicate with the corresponding channel end portions.

Pipes 54 extend through the respective plates 40 and 46 to isolate the flow of coolant into and out of the channels from the flow of reactants. Referring to FIG. 2, the reactant header 18 includes plate 56 which is spaced from plate 40. The pipes 54 extend through plate 56 and plate 40 to thereby provide communication from the cavity 58 of the upstream coolant header 22 to within the channels 38 of the tube bundle. The cavity 58 of the header 22 is defined relative to plate 56 by a continuation of shell 41 and top plate 60.

Similarly with the header configuration of the product header 20, a plate 62 is spaced from the outlet plate 46 through which the pipes 54 extend to provide communication between the outlet portions of the channels 38 of the tube bundle and the downstream header cavity 64. The cavity 64 of the downstream coolant header is defined relative to plate 62 by continuation of the shell 41 and the base portion 66.

Referring to FIG. 4, details of this arrangement for the headers are shown. The channel 38 as partially shown beneath the inlet plate 40 is in communication with pipe 54 which extends through plate 40 and plate 56. The coolant is introduced to the channel 38 via pipe 54 which extends through upper plate 40 and header plate 56. The coolant flows into the header 22 via inlet 30 in the direction of arrow 68 downwardly through the tube 54 into the channel area 38 and along the channel in the direction of arrow 70 to the outlet pipe 54 and to within the cavity 64 in the direction of arrow 72.

The reactants are introduced to the reactant header 18 via inlet 26 where the reactants flow in the direction of arrow 74 into the cavity 76 defined between plates 40 and 56. The reactants flow downwardly of the individual tubes 34 and emerge in the direction of arrow 78 into the cavity 80 defined between plates 46 and 62. The product recovered from the tubes flow in the direction of arrow 78 and exit via outlet 28. In this manner the flows of the reactants into the reactor, the flow of the products out of the reactor and the flow of the coolant are isolated.

It is appreciated that a screen 45 and a screen 47, as shown in FIGS. 4 and 4A may be positioned at the inlet side 14 and the outlet side 16 of the tube bundle to retain the particulate catalyst 82 as noted in FIG. 3 within the tubes of the bundle. It is also appreciated that for some types of reactions, a catalyst coating may be placed on the interior of the tube walls thereby avoiding the need for catalyst particles in the tubes. The tubes of the bundle are all of the same length, because they are essentially each full of the particulate catalyst. It is the catalyst which defines the effective length of a reactive region in each tube in the bundle. In order to provide uniformity in the production conversion and reaction selectivity at the exit of the reactor, then the effective length of each reactive region in each tube must be essentially the same as in all other tubes of the bundle. This feature, in combination with the previously discussed aspect of small radial temperature differences at the outlet of each tube, also assures the uniformity in product conversion and reaction selectivity.

The arrangement according to this invention for the reactor thereby provides a multitubular set-up where the coolant flows co-currently with the reactants. The channels defined between the tubes are discrete and independent of one another so that the coolant flowing through each channel provides a fully co-current flow in heat exchange relationship with the heat generated by the exothermic catalytic reactions in the respective tubes. Preferably a non-boiling coolant is used that is a coolant which has a boiling point well above the highest temperature to which the coolant will rise in flowing through the reactor. By way of co-current circulation of the coolant with the reactants and a non-boiling coolant the temperature and concentration profiles develop symmetrically and gradually along the length of the channels and tubes. This aspect could not be realized in a counter-current flow or cross flow circulation of the coolants relative to the reactants. Therefore, there is no limitation on the size of the tube bundles and according to an aspect of the invention, the tube bundle may comprise 3000 tubes per unit. The metal suitable for the various components of the multitubular reactor (tubes, headers, shell) is carbon steel. Carbon steel shows a good chemical resistance, below 723° K., when contacted with liquid sodium or a sodium-potassium eutectic, two of the possible coolant fluids. If the multitubular pseudoadiabatic reactor requires temperatures of operation higher than 723° K., instead of carbon steel, stainless steel, such as 310SS, can be used for the construction of the unit.

As adapted in the exothermic catalytic conversion of alcohol to gasoline boiling point constituents, carbon steel metal tubes inert to the reaction and temperatures may be about 3 m. in length having an internal tube diameter of approximately 2 to 3 cm. and a wall thickness of approximately 0.25 cm. Since the tube dimension is fairly consistent, they contact each other along their length in the packed bundle to define the channels. As mentioned on the periphery of the tube bundle, barriers may be provided between the tubes and the shell to define the channels through which coolant will flow along the respective exterior surfaces of the tubes. It is also appreciated that in forming the packed bundle barriers could also be provided between adjacent tubes instead of relying on their contacting one another to define the discrete channels.

The apparatus and process may be particulary adapted for use in the catalytic conversion of lower alcohols and particularly methanol into gasoline. Aluminosilicate catalysts are suitable for such reactions as particularly discussed in U.S. Pat. No. 3,928,483 where the crystalline zeolite catalysts ZSM-5, ZSM-11, ZSM-12, ZSM-21 and TEA mordinite catalysts are disclosed which are suitable in the exothermic catalytic conversion of the lower alcohols to gasoline. The preferred catalyst ZSM-5 is particularly suited for the conversion of methanol to gasoline. As applied to the reactor, it has been found that a mean particle diameter of 2 mm. for the catalyst particle is satisfactorty. It is appreciated that in other circumstances for other forms of reactions, other particle sizes may be used. Each tube is filled with the catalyst particles. The estimated pressure drop in the catalyst bed contained in the tubes is negligible as calculated to be 0.0534 atm pressure drop across the 3 m. tubes with repect to a typical total operating pressure between 1 and 3 atm. The internal tube diameter is 2.09 cm. with an external tube diameter of 2.66 cm. The tube bundle is in square pitch format having an equivalent diameter of 0.726 cm. The coolant used is molten sodium having a heat capacity of 0.3108 Kcal/(Kg.°C.), a thermal conductivity of 65.70 Kcal/(m.h.) and a viscosity of 1.175 Kg./(m.h.). Based on experimental data, equations have been developed for the rate of reaction, the limiting temperature for any particular reactant concentration and the limiting partial pressure for the reactor below which pseudoadiabatic reactor conditions are met.

These equations are expressed as follows:

$$T_1 = \frac{a}{b + \ln(A/D)} \quad (1)$$

$$(p_A°)_1 = \frac{A}{B}\left(1 + \frac{C}{D}\right)(T_1 - T_o) \quad (2)$$

$$r = \frac{k_o \exp(-E/RT) p_A}{(1 + 1.5 \, p_A°)} \quad (3)$$

The nomenclature in the above equations is as follows:
A = (M.P. $\rho_b$)/(u. $\rho_g$) (kg.h)/kmol.m)
a = E/R (°K.)
B = ((−$\Delta H_R$). $\rho_b$)/(u.$C_{pg}$. $\rho_g$)) (kg.°K.h)/(kmol.m)
b = natural logarithm of $k_o$
C = (2.U)/(u.$C_{pg}$. $\rho_g R_i$) (1/m)
$C_{pc}$ = heat capacity of the coolant (Kcal/Kg°K.)
$C_{pg}$ = heat capacity of the gas mixture (Kcal/Kg°K.)
D = (2. $\pi.R_i.t_n.U_i$)/($W_c C_{pc}$) (1/m)
E = energy of activation (Kcal/Kmol)
k = thermal conductivity (Kcal/m.h.°K.)
$k_o$ = frequency factor (Kmol/Kg.h.atm)
M = molar mass of the gaseous mixture (kg/kmol)
$p_A$ = partial pressure of methanol (atm)
r = rate of reaction of methanol (kmol/kg.h)
R = universal gas constant (Kcal/Kmol°K.)
$R_i$ = inner tube reactor radius (m)
T = average temperature inside the reactor tubes (°K.)
$T_c$ = temperature of the cooling fluid (°K.)
$T_l$ = limiting temperature defined by Equation (1) (°K.)
$T_o$ = inlet temperature (°K.)
$t_n$ = number of reactor tubes
u = superficial velocity of the gaseous mixture (m/h)
$U_i$ = overall heat transfer coefficient (Kcal/m².h.°K.)
Wc = cooling medium mass flow rate (kg/s)
$\Delta H_R$ = heat of reaction for methanol conversion (Kcal/mol)
$\rho_b$ = bulk density of the fixed bed (Kg/m³)
$\rho_g$ = gas mixture density (Kg/m³)

These equations which are based on experimental data yield the following results. For a methanol feed at an inlet temperature of 613.1° K. the reactant has a heat capacity of 0.5209 Kcal/kg°C., a thermal conductivity of 0.0576 Kcal/(hr.m.°C.), the methanol gas has a density of 0.636 kg./m.³ and a viscosity of 0.072 kg/(m.h).

For a ZSM-5 catalyst diluted five times $k_o$ = exp(13.87); a = E/R = 10555 and the heat of reaction = $H_R$ = −10690 Kcal/Kmol. For these conditions the superficial gas velocity inside each of the reactor tubes at standard atmospheric conditions is 1365 m/h.

Figure 6:
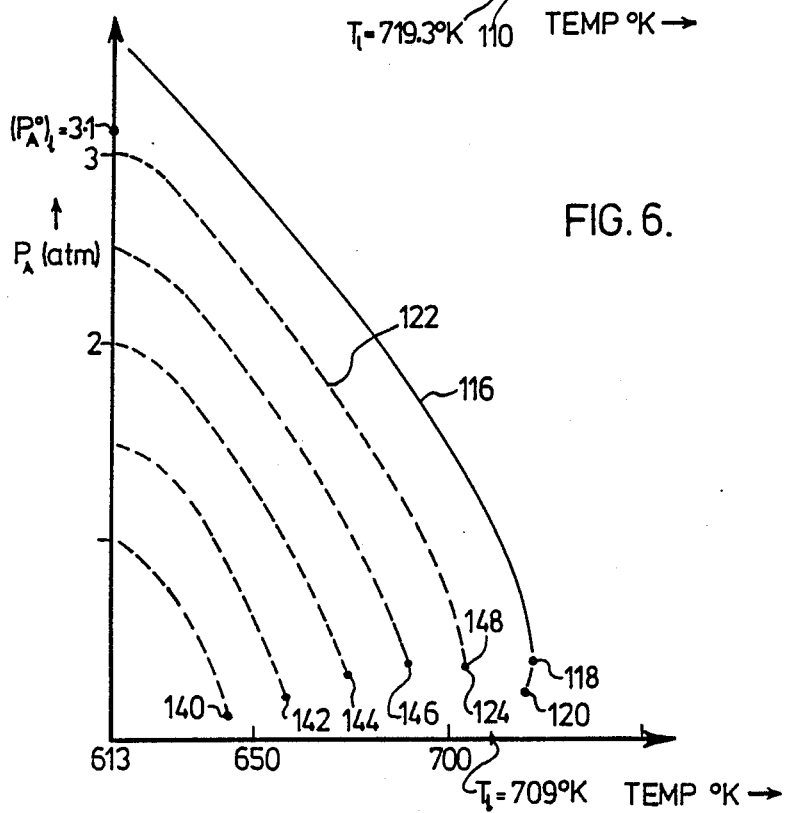
FIG. 6 is a plot similar to FIG. 5 showing the results for various partial pressures of reactant and different coolant flow rate than in FIG. 5.

Applying these conditions to the above equations where the inlet temperature of the coolant is identical to that of the reactants, namely 613.1°, the results are shown in FIGS. 5 and 6. A coolant acceptable for this run is molten sodium. FIG. 5 shows the effect of various partial pressures of the reactants for a coolant flow of rate 10 kg/s. FIG. 6 shows the results for various reactant partial pressures with a coolant flow rate of 20 kg/s. As shown in FIG. 5 for a 10 kg/s coolant flow, $(p_A°)_1$ (the maximum partial pressure for the methanol feed leading to pseudoadiabatic operation) is 1.75 atm. For the higher coolant flow rate the maximum partial pressure of the methanol feed is 3.1 atm. Exceeding these levels as shown in solid line results in hot spots internally of the reactor tube and thus the reactor no longer performs as a pseudoadiabatic reactor. For other coolant flows it is appreciated that other partial pressures for the reactants may be provided to achieve pseudoadiabatic operation. It is also understood that given an inlet reactant partial pressure, there are limiting values for the minimum and maximum coolant flows. The minimum coolant flow occurs when insufficient cooling is provided which results in an internal "hot spot" development and possibly in a run-away condition for the reactor. A maximum coolant flow occurs when for the partial pressure selected the reaction is quenched. An internal "hot spot" of small magnitude is present in this case in a reactor operating with low yields.

According to this arrangement, the operator can monitor the product temperature at the exit of the reactor bundle. Knowing the maximum temperature $T_l$, the operator can immediately realize when the reactor is operating outside the pseudoadiabatic regime when the product temperature exceeds $T_l$. This condition can be corrected by either decreasing the partial pressure of the reactants or increasing the flow of the coolant such that the temperature of the product exiting the tube bundle does not exceed the maximum temperature $T_l$ calculated in accordance with equation 1.

Referring to FIG. 5, conditions where operation of the reactor is outside of the pseudoadiabatic regime are defined by solid lines 100 and 102. For the partial pressures of the methanol feed above 1.75 atm and for the coolant flow at 10 kg/s the temperature along the length of the reactor tube proceeds to a maximum at 104 then reduces to a lesser value at 106. Similarly in curve 102 the temperature proceeds to a maximum 108 compared to an exit temperature of 110. These curves thereby indicate that at these partial pressures of the reactants for the particular coolant flow chosen, "hot spots" have occurred internally of the tube intermediate its length.

On the other hand, with the dotted curves 112 the temperature at the exit indicated at 114 is the maximum which is the desired typical condition to provide the pseudoadiabatic operation. For each dotted line 112, the location of the parameters at reactor exit for the 3 m. length reactor are indicated at 130, 132, 134 and 136. For the solid line 102, the location is indicated at 138. By using Equation (1) and (2), $T_l$ and $(p_A°)$ parameters, characterizing the limiting condition for pseudoadiabatic operation, can be estimated. $T_l$ is estimated at 719.3° K. Similarly in FIG. 6 for a higher coolant flow, curve 116 indicates a higher temperature 118 within the length of the tubes than at exit 120 thereby indicating a "hot spot". The partial pressure for the reactants not to be exceeded in order to provide pseudoadiabatic operation in the reactor is indicated by the $(p_A°)_1$ value of 3.1 atm reported on the ordinate of FIG. 6. Here $T_l$ is approximately 709.3° K. The location of the parameters for curves 122 at reactor exit for a reactor length of 3 m. is indicated at 140, 142, 144, 146 and 148. It is important to mention that both conditions, $(p_A°)_1=1.75$ atm for $W_c=10$ Kg/s and $(p_A°)_1=3.1$ atm for $W_c=20$ Kg/s, provide a high methanol conversion at the exit of a 3 m. reactor length, 0.99 and 0.91 respectively.

At the same time for the condition of curve 112, FIG. 5, the radial temperature profiles at the exit of each one of the tubes of the bundle were assessed using the following equation;

$$T_{centerline} - T_{average} = (T_{average} - T_{coolant})\left(\frac{0.25\ Bi}{1 + 0.25\ Bi}\right) \quad (4)$$

where Bi is the dimensionless Biot number. It was observed that for the curve 112 a Bi=4.2 is estimated and the difference between the centerline and the average temperature at the outlet of the 3 m. tubes is only 0.25° K. This result shows that the total temperature radial difference in each tube is smaller than 1° C. and it confirms the concept presented in the present invention that the monitoring of the average temperature at the reactor outlet and its comparison with $T_l$ is an adequate basis to control that the operation of a multitubular reactor takes place under the pseudoadiabatic regime.

The reactor and process according to this invention as applied to exothermic catalytic reactions overcomes a number of the problems associated with the former fixed bed catalytic reactors and fluidized bed reactors and provides an economical configuration. The reactor has wide application in the exothermic catalytic conversion of various reactants as presently carried out in existing fixed bed and fluidized bed catalytic reactors. The system provides for ease of operation in controlling and monitoring the reaction and responding to changes in the reaction as the system operates over time. The reactor operator is able to determine by way of Equations (1) and (2) for any selected coolant flow rate, the limiting value for the partial pressure of the reactant and the maximum temperature $T_l$ for the product stream emerging from the reactor. The operator can then choose a reactant partial pressure in the feed stream as close as he may desire to the maximum limiting valve $(p_A°)_1$ and then monitor the temperature of the emerging product stream once the reactor achieves steady state operation. If the sensed temperature is above $T_l$, then he knows immediately that a "hot spot" has developed somewhere along the length of the reactor. The operator can then tune the reactor by gradually reducing the partial pressure of the reactant in the feed stream until the sensed temperature is below $T_l$. Alternatively, and as previously explained, in some situations it may be easier to increase the coolant flow rate until the sensed temperature falls below the $T_l$.

While preferred embodiments have been described and illustrated herein, the person skilled in the art will appreciate that changes and modifications may be made therein without departing from the spirit and scope of this invention as defined in the appended claims.

The embodiments of the invention in which an exclusive property or privilege is claimed are defined as follows:

1. A pseudoadiabatic process for exothermic catalytic conversion of gasoline constituent forming reactants including $C_1$ to $C_3$ alcohols, conducted in a multi-tubular catalytic reactor, wherein the reactor includes a bundle of parallel tubes having inlet and outlet ends and a consistent confined volume of catalyst within each of the tubes along their length, each of said tubes being continuous along its length and independent of all other tubes and having effective reactive regions therein all of essentially the same length as defined by said consistent confined volume of catalyst in each of said tubes, each tube further having an inlet and an outlet side, and means defining a discrete channel along adjacent tubes of the bundle to provide thereby a plurality of channels through the bundle where each tube of the bundle is in contact with a coolant flowing in one or more of said channels, said plurality of channels having an inlet side and an outlet side, wherein said process comprises:

passing said reactants at a known preselected concentration through said bundle of parallel tubes wherein the inlet temperature is high enough to initiate said catalytic conversion throughout said volume of catalyst;

introducing said coolant to said discrete channels at a temperature substantially the same as the inlet temperature of said reactants and passing said coolant through each of said discrete channels in a direction co-current with the direction of flow of said reactants through said bundle of tubes at a preselected flow rate sufficient to substantially match the temperature rise of the catalytic conversion reaction for the partial pressure of reactants selected and the heat transfer characteristics of the catalyst and said tubes so that the coolant is substantially the same temperature as the temperature of the reaction product stream leaving the outlet of the tubes containing the confined volume of catalyst substantially encompassing the reaction time, said outlet temperature not exceeding a preselected maximum temperature suitable for maximum conversion of said reactants into desired reaction product without the need for recycle of the reaction product and unreacted reactants to achieve further conversion;

sensing the temperature of reaction products at said outlet side of said tube bundle; and varying either said partial pressure of reactants or said coolant flow rate to maintain said sensed temperature to said highest temperature level at said outlet side.

* * * * *